(12) United States Patent
Nagai et al.

(10) Patent No.: US 8,094,883 B2
(45) Date of Patent: Jan. 10, 2012

(54) SLEEPINESS LEVEL DETERMINATION DEVICE FOR DRIVER

(75) Inventors: Fumiya Nagai, Anjo (JP); Takuhiro Omi, Anjo (JP)

(73) Assignee: DENSO CORPORATION, Kariya (JP)

( * ) Notice: Subject to any disclaimer, the term of this patent is extended or adjusted under 35 U.S.C. 154(b) by 744 days.

(21) Appl. No.: 12/285,580

(22) Filed: Oct. 9, 2008

(65) Prior Publication Data

US 2009/0097701 A1   Apr. 16, 2009

(30) Foreign Application Priority Data

Oct. 11, 2007   (JP) ................ 2007-265764

(51) Int. Cl.
*G06K 9/00* (2006.01)
(52) U.S. Cl. ..................... 382/103; 340/573.7
(58) Field of Classification Search ............ 382/100, 382/103, 106, 107, 118, 181, 190, 195, 203, 382/206; 340/575, 576, 573.1, 573.7; 351/205, 351/206, 209, 210
See application file for complete search history.

(56) References Cited

U.S. PATENT DOCUMENTS

| | | | | |
|---|---|---|---|---|
| 5,465,079 A | * | 11/1995 | Bouchard et al. | 340/576 |
| 5,573,006 A | * | 11/1996 | Shimotani et al. | 600/558 |
| 5,798,695 A | * | 8/1998 | Metalis et al. | 340/576 |
| 6,097,295 A | * | 8/2000 | Griesinger et al. | 340/576 |
| 7,791,491 B2 | * | 9/2010 | Johns | 340/576 |
| 7,821,409 B2 | * | 10/2010 | Ishida | 340/576 |
| 7,948,387 B2 | * | 5/2011 | Ishida et al. | 340/575 |

FOREIGN PATENT DOCUMENTS

| | | |
|---|---|---|
| JP | A-10-119606 | 5/1998 |
| JP | A-10-272959 | 10/1998 |
| JP | A-2000-60799 | 2/2000 |
| JP | A-2002-279410 | 9/2002 |
| JP | A-2006-109980 | 4/2006 |
| JP | A-2006-174960 | 7/2006 |
| JP | A-2007-233475 | 9/2007 |
| JP | A-2007-241937 | 9/2007 |

OTHER PUBLICATIONS

Office Action mailed May 11, 2010 in corresponding Japanese patent application No. 2007-265764 (and English translation).
Hiroki Kitajima et al., "Study for an estimating method of sleepiness while driving a vehicle," *Transaction of the Japan Society of Mechanical Engineers*, No. 96,1780, Nov. 22, 1996.
Notice of Reason for Refusal mailed on Nov. 4, 2009, issued from the Japanese Patent Office in the corresponding Japanese patent application No. 2007-265764 (and English translation).

* cited by examiner

*Primary Examiner* — Anand Bhatnagar
(74) *Attorney, Agent, or Firm* — Posz Law Group, PLC

(57) ABSTRACT

A sleepiness level determination device includes: a detector processing a face image of an user and for detecting an eye image of the user based on the face image; a characteristic value calculating unit calculating a characteristic value regarding the eye based on the eye image; a sleepiness level determining unit determining a sleepiness level based on the characteristic value; and a reliability calculating unit calculating reliability of the sleepiness level based on the characteristic value.

11 Claims, 5 Drawing Sheets

FIG. 5
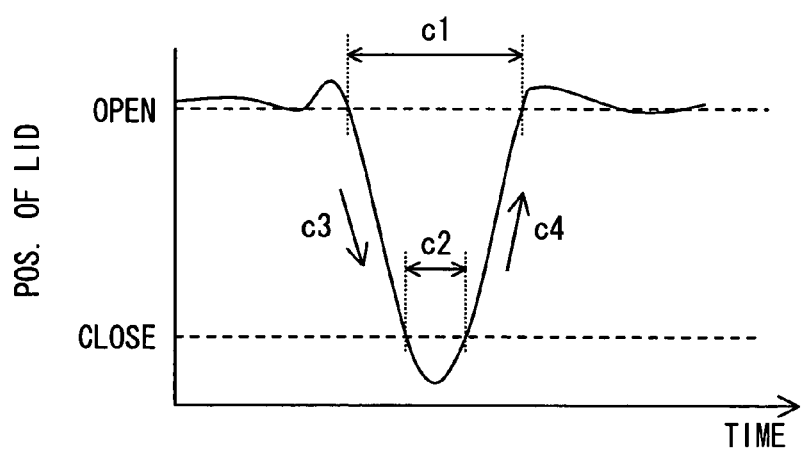
FIG. 6A     FIG. 6B     FIG. 6C
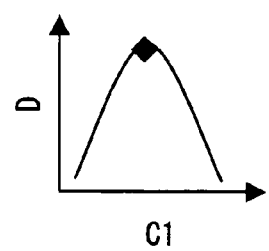
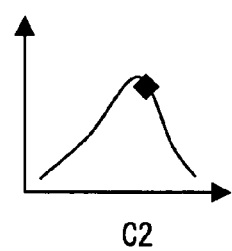
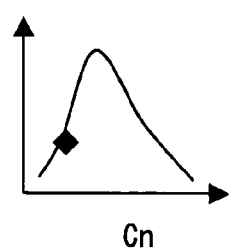

FIG. 7

| SLEEPINESS LEVEL | DRIVER'S CONDITION | BEHAVIOR |
|---|---|---|
| 1 | NOT SLEEPY | ·LINE OF SIGHT MOVES QUICKLY AND FREQUENTLY<br>·PERIOD OF BLINK IS STABLE<br>·EYE MOVES ACTIVELY TOGETHER WITH BODY MOTION |
| 2 | SLIGHTLY SLEEPY | ·LINE OF SIGHT MOVES SLOWLY<br>·LIPS OPEN |
| 3 | SLEEPY | ·BLINK IS SLOW AND FREQUENTLY<br>·DRIVER MOVES HIS MOUTH<br>·DRIVER RESEATS HIMSELF<br>·DRIVER PUTS HIS HAND ON HIS FACE |
| 4 | RATHER SLEEPY | ·DRIVER BLINKS CONSCIOUSLY.<br>·DRIVER MOVES HIS BODY SENSELESSLY. FOR EXAMPLE, HE SHAKES HIS HEAD, AND HE MOVES HIS SHOULDER UP AND DOWN<br>·DRIVER YAWNS FREQUENTLY, AND TAKES A DEEP BREATH OFTEN<br>·BLINK AND MOVEMENT OF LINE OF SIGHT ARE VERY SLOW |
| 5 | VERY SLEEPY | ·DRIVER CLOSES HIS EYE<br>·DRIVER NODS HIS HEAD FORWARD AND/OR BACKWARD |

SLEEPINESS LEVEL DETERMINATION DEVICE FOR DRIVER

CROSS REFERENCE TO RELATED APPLICATION

This application is based on Japanese Patent Application No. 2007-265764 filed on Oct. 11, 2007, the disclosure of which is incorporated herein by reference.

FIELD OF THE INVENTION

The present invention relates to a sleepiness level determination device for a driver of a vehicle.

BACKGROUND OF THE INVENTION

A method for estimating sleepiness level of a driver of a vehicle based on low awake state is proposed to prevent the driver from dozing off at the wheel. For example, the sleepiness level is detected by detecting movement of an eye of the driver such as blink or eyelid's movement. Firstly, the movement of the eye is detected when the driver clearly awakes, for example, when the driver drives the vehicle in the early stages of the driving. The movement of the eye is compared with the early stages, so that the sleepiness level is detected.

The estimation of the sleepiness level may deviate from proper value because of individual variation and detection error. Therefore, an arousal information display device disclosed in JP-A-2006-174960 calculates detection reliability of image processing based on reliability of estimation of awake level (i.e., arousal level). Both of the detection reliability and the arousal level are presented to the driver. Thus, the driver can recognize that the arousal level is not proper when an improper arousal level is presented.

However, the above arousal information display device detects the reliability by obtaining a detection time ratio corresponding to a time for detecting the driver's eye image from an image. Therefore, the performance of the image processor and the influence of disturbance of outside light may affect the calculation of the reliability. Thus, the reliability may depend on a factor other than detection of the arousal level. Accordingly, the reliability of estimation of the arousal level may be not proper.

SUMMARY OF THE INVENTION

In view of the above-described problem, it is an object of the present disclosure to provide a sleepiness level determination device for a driver of a vehicle.

According to an aspect of the present disclosure, a sleepiness level determination device includes: a detector processing a face image of an user and for detecting an eye image of the user based on the face image; a characteristic value calculating unit calculating a characteristic value regarding the eye based on the eye image; a sleepiness level determining unit determining a sleepiness level based on the characteristic value; and a reliability calculating unit calculating reliability of the sleepiness level based on the characteristic value.

In the above device, the reliability of the sleepiness level is determined based on a statistics of the characteristic value of the eye. Thus, the reliability is calculated based on determination of the sleepiness level itself. Thus, the reliability is determined with high accuracy.

BRIEF DESCRIPTION OF THE DRAWINGS

The above and other objects, features and advantages of the present invention will become more apparent from the following detailed description made with reference to the accompanying drawings. In the drawings:

FIG. 5 is a graph showing a relationship between time and a position of an eyelid;

FIGS. 6A to 6C are graphs showing frequency distribution;

FIG. 7 is a diagram showing a relationship among sleepiness level, driver's condition and behavior.

DETAILED DESCRIPTION OF THE PREFERRED EMBODIMENTS

Figure 1:
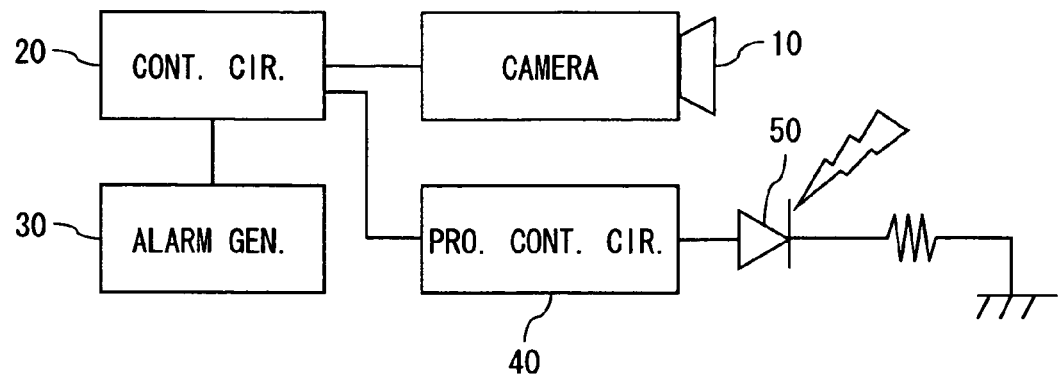
FIG. 1 is a block diagram showing a sleepiness level determination device.

A sleepiness level determination device according to an example embodiment of the present disclosure will be explained. The device detects a sleepiness level of a driver of a vehicle. As shown in FIG. 1, the device includes a camera 10, a control circuit 20, an alarm generator 30, a projector control circuit 40 and a projector 50.

Figure 2:
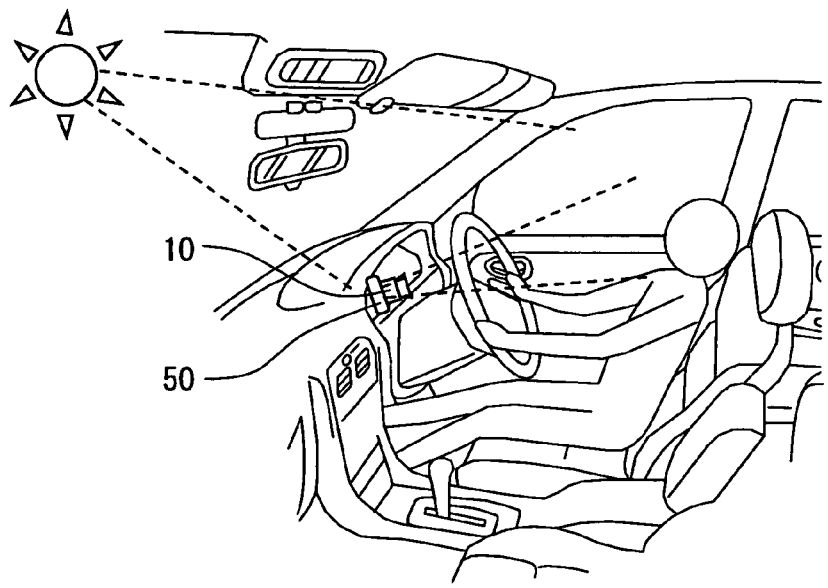
FIG. 2 is a schematic view showing a camera and a projector in a compartment of a vehicle.

The camera 10 takes a picture of a face image of the driver, as shown in FIG. 2. The camera 10 is arranged around an instrument panel of a compartment of the vehicle. The camera 10 includes an imager for shooting pictures with high speed. Thus, the camera 10 can shoot a picture with a shooting time of about 300 micro seconds per one frame and a shooting interval of about 30 micro seconds.

The control circuit 20 stores image information of the face image shot by the camera 10 in an image memory (not shown). The control circuit 20 reads out the image information from the image memory, so that the control circuit 20 executes an image processing for detecting an eye image of the driver from the face image. Further, the control circuit 20 executes a process for calculating characteristic value relating to the eye based on the eye image. The projector control circuit 40 adjusts irradiation of the projector 50. The control circuit 20 controls a shooting timing of the camera 10 in synchronization with adjustment of the irradiation of the projector 50 by the projector control circuit 40. Furthermore, the camera 10 adjusts exposure time of the camera 10 and an output gain of the camera 10.

The control circuit 20 determines, i.e., estimates sleepiness level of the driver based on the characteristic value regarding the eye of the driver. The reliability of determination of the sleepiness level is calculated based on the statistics of the characteristic value of the eye. The control circuit 20 determines based on the reliability of the sleepiness level whether alarm for the driver in accordance with the sleepiness level is performed.

The alarm generator 30 includes an amplifier and a speaker arranged at an appropriate position of the compartment. The alarm generator 30 generates alarm such as alarm sound and alarm voice message according to an input signal from the control circuit 20.

Figure 3:
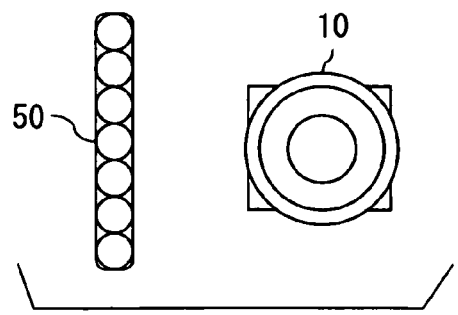
FIG. 3 is a schematic view showing a driver's sight of the camera and the projector.

The projector control circuit 40 controls light amount, i.e., strength of light from the projector and turns on and off the projector, which is arranged in parallel to the camera 10, as shown in FIG. 3. The projector control circuit 40 controls the irradiation state of the light to irradiate the light on the face of the driver in synchronization with the shoot timing of the camera 10.

The projector 50 includes multiple light sources for emitting light such as infrared light and near-infrared light having center wavelength in a range between 850 nm and 950 nm. Multiple light sources are aligned along with a vertical direction of the face of the driver. Each light source emits the light toward the face of the driver.

Figure 4:
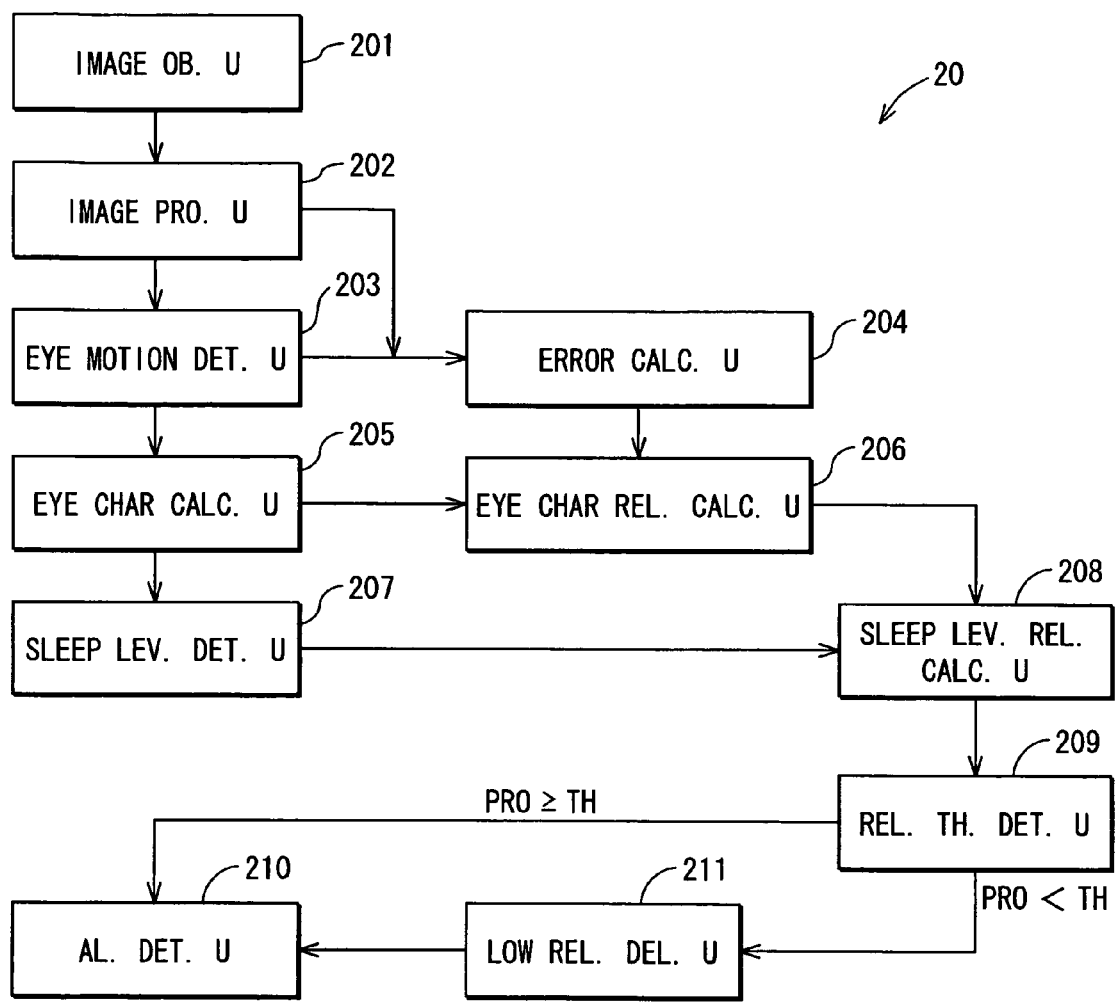
FIG. 4 is a block diagram showing a control circuit.

The operation of the sleepiness level determination device will be explained. FIG. 4 shows functions of the control circuit 20. An image obtaining unit 201 obtains the image information of the face image shot by the camera 10. An image processing unit 202 executes the image processing step to detect the image of the eye of the driver from the face image, which is obtained by the image obtaining unit 201. An eye movement, i.e., the eye motion detection unit 203 detects a height of an eyelid for detecting an opening degree of the eye and a line of sight based on the eye image detected by the image processing unit 202. The line of sight may be defined as a part of the compartment of the vehicle, at which the driver directs his eyes. For example, the part of the vehicle is a windshield, a rearview mirror, a side mirror and the like. Here, when the part of the vehicle is the windshield, the driver directs his eyes toward the front of the vehicle.

A detection error calculating unit 204 for detecting error of the image processing step. Specifically, the calculating unit 204 generates a flag in each frame of the eye image. The flag shows whether the eye motion detection unit 203 does not detects the motion of the eye in the frame because of behavior of the driver and the influence of the outside light. In view of the flag, it is determined whether the eye motion detection unit 203 detects the eye motion in the frame.

An eye characteristic value calculating unit 205 calculates characteristic values of each blink such as a period of time $c1$ from the start to the end of one blink, a time interval $c2$ of closing the eye, a closing speed $c3$ of the eyelid and an opening speed $c4$ of the eyelid. Further, the eye characteristic value calculating unit 205 calculates a position of the line of sight, the number of blinks per unit time, average of opening degree per unit time, average of closing degree per unit time, time interval while the line of sight ceases. Thus, different characteristic values $c1$ to $cn$ (n represents natural number, i.e., n=1, 2, ... i) regarding the eye are calculated. When the flag of one frame represents yes, the characteristic values cannot be calculated in the one frame. Thus, the characteristic values of the one frame are obtained by complementing those of adjacent frames.

A reliability calculating unit 206 for eye characteristic value calculates the reliability of the characteristic value of the eye. Specifically, the reliability calculating unit 206 calculates a detection rate of each blink. In FIG. 5, the period of time $c1$ from the start to the end of one blink is defined as one blink interval. The one blink interval includes multiple frames. A detection rate E is defined as a ratio between the number of frames having the flag of "yes" and the number of the whole frames in the one blink interval. The detection rate E is in a range between 0 and 1.

A sleepiness level determining unit 207 determines, i.e., estimates a sleepiness level D based on a regression equation f having multiple explaining variables of the characteristic values $c1$ to $cn$. The regression equation f is an estimation function. The estimation function f is expressed as follows.

$$D = f(c1, c2, \ldots, cn) \tag{F1}$$

The estimation function f is obtained by setting the characteristic values $c1, \ldots, cn$ based on experimental results in view of a relationship between the sleepiness level D (=1, 2, 3, 4, or 5) and a corresponding behavior of the driver. In FIG. 7, the characteristics of the driver's behavior are defined in a corresponding sleepiness level. As the sleepiness level is higher, the driver feels sleepier. The sleepiness level D is determined based on multiple different characteristic values regarding the eye of the driver, so that robustness of determination of the sleepiness level becomes high.

A reliability calculating unit 208 for the sleepiness level calculates frequency distribution of all characteristic values $c1, \ldots, cn$ in each sleepiness level D when the sleepiness level determining unit 207 estimates the sleepiness level D. Further, the reliability calculating unit 208 determines a representative characteristic value $x1$ to $xn$ in each characteristic value $c1$ to $cn$. The representative characteristic value $x1$ to $xn$ represents a respective frequency distribution. The representative characteristic value $x1$ to $cn$ is a main value of the distribution such as average of the distribution and a center value of the distribution.

The reliability calculating unit 208 calculates the reliability R of the sleepiness level D based on proximity between the representative characteristic values $x1$ to $xn$ and the characteristic values $c1$ to $cn$. The representative characteristic values $x1$ to $xn$ in each sleepiness level D are preliminarily determined. The characteristic values $c1$ to $cn$ are calculated by the eye characteristic value calculating unit 205 when the sleepiness level determining unit 207 estimates the sleepiness level D.

Specifically, as shown in FIGS. 6A to 6C, for example, when the sleepiness level D $(=f(c1, c2, \ldots, cn))$ is three, the proximity between the characteristic value $c1$ to $cn$ and the corresponding representative characteristic value $x1$ to $xn$ in the corresponding frequency distribution. In FIGS. 6A to 6C, square dots represents the detected characteristic values in the frequency distribution. The reliability R is calculated by the following formula F2 with considering the detection ratio E.

$$R = \{[k1 \times (\text{proximity between } c1 \text{ and } x1) + [k2 \times (\text{proximity between } c2 \text{ and } x2) + \ldots + [kn \times (\text{proximity between } cn \text{ and } xn)]\} \times E \tag{F2}$$

Here, $k1$ to $kn$ are determined in proportion to contribution ratios of the characteristic values $c1$ to $cn$ when the sleepiness level D is determined. The contribution ratio is a standard of the reliability of the regression equation when the sleepiness level D is estimated with the regression equation.

The proximity between the characteristic value $c1$ to $cn$ and the corresponding representative characteristic value $x1$ to $xn$ may be described with dispersion $\sigma$. For example, when the distribution of the characteristic values $c1$ to $cn$ is a normal distribution, and the characteristic value is disposed within $\pm 1\sigma$, the proximity (i.e., the weight) is set to "1." When the characteristic value is disposed within $\pm 2\sigma$, the proximity is set to "½." When the characteristic value is disposed within $\pm 3\sigma$, the proximity is set to "⅓." When the characteristic value is not disposed within $\pm 3\sigma$, the proximity is set to "0."

The reliability R of the sleepiness level D is calculated based on the proximity (i.e., plausibility) of each characteristic value $c1$ to $cn$ when the sleepiness level D is estimated, with regard to the representative characteristic values $x1$ to $xn$ for representing the distribution of the characteristic values $c1$ to $cn$. Thus, the reliability R properly corresponds to the reliability of the sleepiness level D.

A reliability threshold determining unit 209 determines, i.e., specifies the characteristic value $c1$ to $cn$ having low proximity, which is lower than a proximity threshold. For example, the proximity threshold is "1," and therefore, a predetermined characteristic value is disposed within $\pm 1\sigma$. The proximity threshold provides a standard as high reliability. When the characteristic values $c1$ to $cn$ includes the low reliability characteristic value having the proximity smaller than the proximity threshold, a low reliability deleting unit 211 determines the sleepiness level with deleting the low reliability characteristic values. Specifically, the low reliability deleting unit 211 deletes the characteristic value having low reliability, and calculates the sleepiness level D' by using the estimation function f without the low reliability characteristic value. For example, when the characteristic values c1 to cn includes only one the low reliability characteristic value ci, the estimation function f is described as follows.

$$D'=f(c1,c2,\ldots,ci-1,ci+1,\ldots,cn) \tag{F3}$$

When the sleepiness level D is three, i.e., when D=f(c1, c2, . . . , cn)=3, the sleepiness level D' without the low reliability characteristic value may be 3.5, i.e., $$D'=f(c1,c2,\ldots,ci-1,ci+1,\ldots,cn)=3.5.$$

Thus, by removing the low reliability characteristic value from factors for determining the sleepiness level, the sleepiness level can be estimated with high accuracy.

An alarm determining unit 210 determines whether alarm sound and/or alarm voice message corresponding to the sleepiness level D, D' is formed and is output to the driver. At this time, the alarm determining unit 210 determines based on the reliability R. For example, when the sleepiness level D is equal to or larger than three, and further, when the reliability R for one minute is equal to or larger than 90%, the alarm determining unit 210 determines that the alarm sound and/or the alarm voice message is output. Thus, the driver's feeling with respect to the alarm is relaxed. The alarm may be generated not only with using sound but also with using display and vibration.

The sleepiness level determination device determines the sleepiness level D based on the characteristic values c1 to cn. Specifically, the statistics of the characteristic values c1 to cn provides the frequency distribution. The representative characteristic values x1 to xn represent the frequency distribution. The sleepiness level determination device calculates the reliability R of the sleepiness level D based on the proximity between the representative characteristic values x1 to xn and the characteristic values c1 to cn. Thus, the reliability R is calculated with respect to the determination of the sleepiness level D itself. The reliability of determination of the sleepiness level D is improved.

(Modifications)

Figure 8:
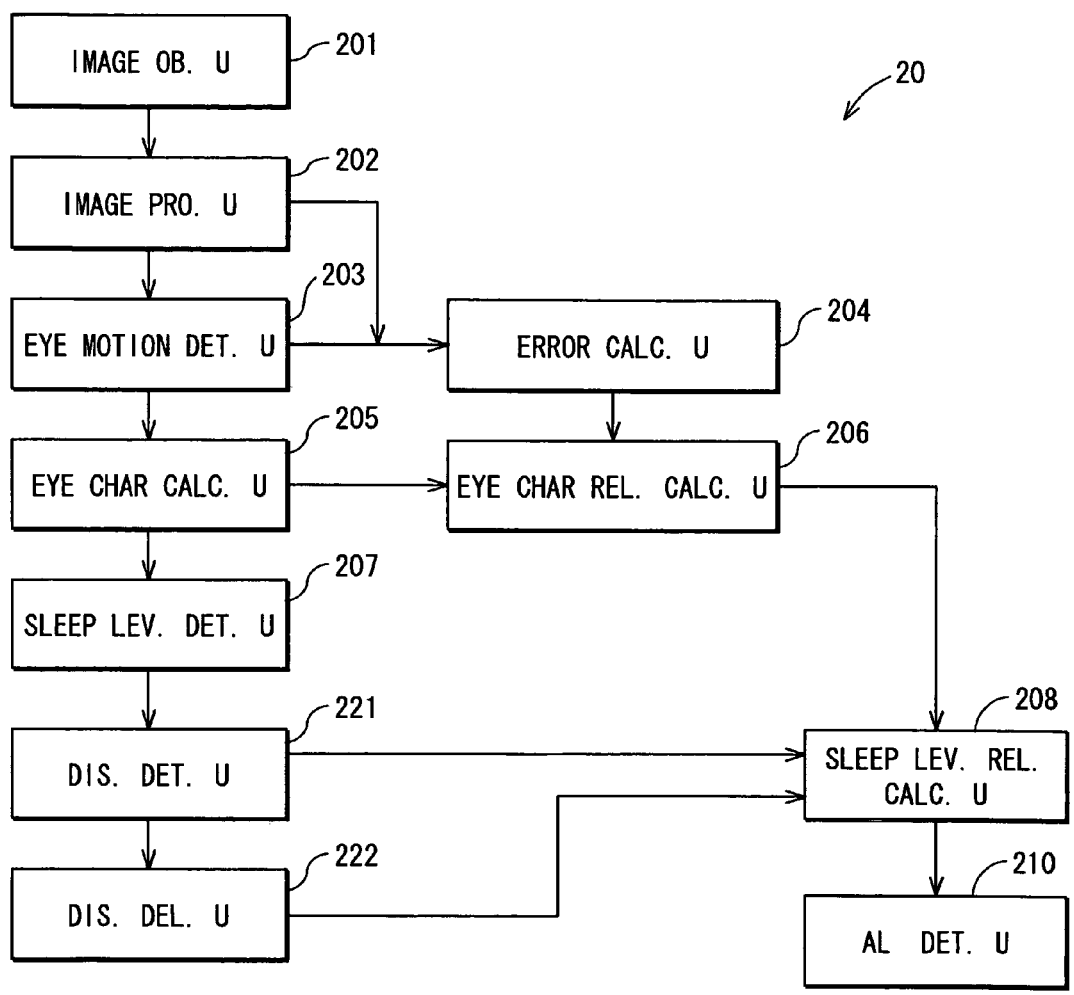
FIG. 8 is a block diagram showing a control circuit according to a modification of an example embodiment.

FIG. 8 shows a control circuit 20 according to a modification of the example embodiment. The circuit 20 in FIG. 8 does not include the reliability threshold determining unit 209 and the low reliability deleting unit 211. The circuit 20 includes a discrepancy determining unit 221 for the sleepiness level and a discrepancy deleting unit 222, which determines the sleepiness level with removing the discrepancy.

The sleepiness level determining unit 207 determines the sleepiness level D from the formula F1. Further, the sleepiness level determining unit 207 estimates, i.e., determines an individual sleepiness level D1 to Dn from each characteristic value c1 to cn. The discrepancy determining unit 221 compares the individual sleepiness levels D1 to Dn, so that the unit 221 determines whether an inconsistence individual sleepiness level exists. When the individual sleepiness levels D1 to Dn includes the inconsistence individual sleepiness level, the discrepancy deleting unit 222 determines the sleepiness level D" by using the estimation function f without the characteristic value c1 to cn corresponding to the inconsistence individual sleepiness level D1 to Dn. For example, the first individual sleepiness level D1 is three, i.e., D1=f(c1)=3. The second individual sleepiness level D2 is three, i.e., D2=f(c2)=3. The n-th individual sleepiness level Dn is one, i.e., Dn=f(cn)=1. In this case, the n-th individual sleepiness level Dn calculated based on the n-th characteristic value cn is different from the other individual sleepiness levels D1 to Dn-1. Thus, the sleepiness level D" is calculated by using the following formula F4. Specifically, the sleepiness level D" is calculated by the estimation function f without using the n-th characteristic value cn.

$$D''==f(c1,c2,\ldots,cn-1) \tag{F4}$$

When the sleepiness level D is three, i.e., when D=f(c1, c2, . . . , cn)=3, the sleepiness level D" without the inconsistence individual sleepiness level may be 3.5, i.e., D"=f(c1, c2, . . . , cn-1)=3.5.

Here, when the individual sleepiness levels D1 to Dn are different from each other, or when it is difficult to specify the inconsistence individual sleepiness level such that, for example, the first individual sleepiness level D1 is three, the second individual sleepiness level D2 is three, the third individual sleepiness level D3 is two, and the fourth individual sleepiness level D4 is two, the inconsistence individual sleepiness level may be specified in view of a contribution rate of each characteristic value to the estimation function f.

The reliability calculating unit 208 for the sleepiness level calculates the reliability R" based on the characteristic values c1 to cn-1 without using the characteristic value cn corresponding to the inconsistence individual sleepiness level Dn, the contribution rate of the characteristic values c1 to cn-1, and the detection rate E according to the following formula F5.

$$R''=\{[k1\times(\text{contribution rate of } c1)+[k2\times(\text{contribution rate of } c2)+\ldots+[kn-1\times(\text{contribution rate of } cn-1)]\}\times E$$

The reliability R" of the sleepiness level D" is calculated from the contribution rate of each characteristic value c1 to cn-1, which are used in the determination of the sleepiness level D". The contribution ratio is a standard of the reliability of the regression equation when the sleepiness level D" is estimated with the regression equation. Thus, the calculated reliability R" properly corresponds to the reliability of the sleepiness level D".

Further, the inconsistence individual sleepiness level is removed from the elements of calculation of the reliability R" and estimation of the sleepiness level D". Thus, the device determines the sleepiness level D" and the reliability R" with high accuracy.

In the above example embodiment, the reliability R of the sleepiness level D is calculated in view of the detection rate E, which is calculated by the detection error calculating unit 204. Alternatively, the reliability R of the sleepiness level D may be calculated without using the detection rate E. Specifically, the reliability R may be calculated with using only the statistics of the characteristic values c1 to cn. Even when the detection rate E is not used, the reliability R may properly correspond to the reliability of the sleepiness level D.

While the invention has been described with reference to preferred embodiments thereof, it is to be understood that the invention is not limited to the preferred embodiments and constructions. The invention is intended to cover various modification and equivalent arrangements. In addition, while the various combinations and configurations, which are preferred, other combinations and configurations, including more, less or only a single element, are also within the spirit and scope of the invention.

What is claimed is:

1. A sleepiness level determination apparatus comprising:
    a detecting device for performing a predetermined image processing on a face image, which is shot at predetermined shooting time intervals and shows a face of a driver, and for detecting an eye image based on the face image;
    a characteristic value calculating device for calculating a plurality of different characteristic values of eye based on the eye image detected by the detecting device, the characteristic values of eye including a period of time from a start to an end of one blink, a time interval of closing an eye, a closing speed of an eyelid, and an opening speed of the eyelid;
    a sleepiness level determining device for determining a sleepiness level among a plurality of sleepiness levels, based on a predetermined estimation function having the plurality of different characteristic values of eye as a plurality of explaining variables calculated by the characteristic value calculating device;
    a representative characteristic value determining device for obtaining a distribution of each characteristic value of eye with respect to every sleepiness level when the sleepiness level determining device determines the sleepiness level and for determining a representative characteristic value with respect to each distribution; and
    a reliability calculating device for calculating reliability of the sleepiness level determined by the sleepiness level determining device according to proximity between each characteristic value of eye at a time when the sleepiness level is determined and a corresponding representative characteristic value determined by the representative characteristic value determining device with respect to the sleepiness level determined by the sleepiness level determining device.

2. The sleepiness level determination apparatus according to claim 1, further comprising:
    a contribution ratio calculating device for calculating a contribution ratio of each characteristic value of eye when the sleepiness level determining device determines the sleepiness level,
    wherein the reliability calculating device calculates the reliability of the sleepiness level based on the contribution ratio of each characteristic value of eye when the sleepiness level is determined.

3. The sleepiness level determination apparatus according to claim 2,
    wherein the sleepiness level determining device determines an individual sleepiness level with respect to each characteristic value of eye,
    the apparatus further comprising:
    an inconsistence characteristic value specifying device for specifying an inconsistence characteristic value among the plurality of different characteristic values of eye,
    wherein the inconsistence characteristic value has the individual sleepiness level determined by the sleepiness level determining device, which is not consistent with other individual sleepiness levels,
    wherein the sleepiness level determining device finally determines the sleepiness level based on the plurality of characteristic values other than the inconsistence characteristic value specified by the inconsistence characteristic value specifying device, and
    wherein the reliability calculating device finally calculates the reliability of the sleepiness level based on the contribution ratio of each characteristic value other than the inconsistence characteristic value specified by the inconsistence characteristic value specifying device.

4. The sleepiness level determination apparatus according to claim 1, further comprising:
    a low reliability characteristic value specifying device for specifying a characteristic value of eye among the plurality of different characteristic values of eye, the characteristic value of eye having the proximity between each characteristic value of eye at a time when the sleepiness level is determined and a corresponding representative characteristic value, and the proximity being larger than a predetermined threshold proximity, which provides a high reliability threshold,
    wherein the sleepiness level determining device finally determines the sleepiness level based on the plurality of characteristic values other than the characteristic value specified by the low reliability characteristic value specifying device.

5. The sleepiness level determination apparatus according to claim 4,
    wherein the characteristic value specified by the low reliability characteristic value specifying device is a low reliability characteristic value, and
    wherein, when the characteristic value has the proximity equal to or smaller than the predetermined threshold proximity, individual reliability corresponding to each characteristic value is equal to or higher than a predetermined individual reliability.

6. The sleepiness level determination apparatus according to claim 5,
    wherein the representative characteristic value of each distribution is one of average, median and mode of a corresponding distribution,
    wherein the distribution of each characteristic value has a dispersion, which is defined as $\sigma$, and
    wherein the proximity of each characteristic value is defined in such a manner that, the proximity is one when the characteristic value is disposed within $\pm 1\sigma$, the proximity is one-half when the characteristic value is disposed within $\pm 2\sigma$, the proximity is one-third when the characteristic value is disposed within $\pm 3\sigma$, and the proximity is zero when the characteristic value is not disposed within $\pm 3\sigma$.

7. The sleepiness level determination apparatus according to claim 1, further comprising:
    a detection ratio calculating device for calculating a detection ratio of the eye image by the detecting device,
    wherein the reliability calculating device calculates the reliability of the sleepiness level based on the characteristic value in addition to the detection ratio calculated by the detection ratio calculating device.

8. The sleepiness level determination apparatus according to claim 7, further comprising:
    a camera shooting the face image, wherein the camera shoots a plurality of frames during a blink; and
    a detection error calculating device detecting error of the image processing of the detector in each frame,
    wherein, when the detection error calculating device does not detect error in a frame, the frame is defined as a detected frame, and
    wherein the detection ratio is a ratio between the number of detected frames and the number of a whole frames.

9. The sleepiness level determination apparatus according to claim 1,
    wherein the plurality of characteristic values are independent from each other, and wherein the representative characteristic value represents a corresponding distribution.

10. The sleepiness level determination apparatus according to claim 1,
wherein the sleepiness level determining device determines the sleepiness level based on the characteristic value by using a regression equation.

11. The sleepiness level determination apparatus according to claim 1, further comprising:
a contribution ratio calculating device calculating a contribution ratio of each characteristic value with respect to the sleepiness level; and
a detection ratio calculating device calculating a detection ratio of the eye image,
wherein the number of the plurality of characteristic values is defined as n, the reliability is defined as R, the contribution of each characteristic value is in proportion to Ki, the proximity of each characteristic value is defined as Pi, and the detection ratio is defined as E, and
wherein the reliability calculating device calculates the reliability based on the proximity, the contribution ratio and the detection ratio of each characteristic value according to an equation of:

$$R = \{[K1 \times P1 + \ldots + Kn \times Pn]\} \times E.$$

* * * * *